US007005253B2

(12) United States Patent
Polyak et al.

(10) Patent No.: US 7,005,253 B2
(45) Date of Patent: Feb. 28, 2006

(54) COLD STORAGE SOLUTION FOR ORGAN AND BIOLOGICAL TISSUE PRESERVATION

(75) Inventors: Maximilian Polyak, Glenmoore, PA (US); Ben O'Mar Arrington, 1116 Mount Tom Rd., East Stroudsburg, PA (US) 18301

(73) Assignee: Ben O'Mar Arrington, East Stroudsburg, PA (US)

( * ) Notice: Subject to any disclaimer, the term of this patent is extended or adjusted under 35 U.S.C. 154(b) by 77 days.

(21) Appl. No.: 09/976,804

(22) Filed: Oct. 12, 2001

(65) Prior Publication Data

US 2002/0064768 A1 May 30, 2002

Related U.S. Application Data

(60) Provisional application No. 60/240,023, filed on Oct. 13, 2000.

(51) Int. Cl.
*A01N 1/00* (2006.01)
(52) U.S. Cl. .......................................... 435/1.1; 435/1.2
(58) Field of Classification Search ................ 435/1.1, 435/1.2, 1.3, 2
See application file for complete search history.

(56) References Cited

U.S. PATENT DOCUMENTS

| | | | |
|---|---|---|---|
| 4,798,824 A | 1/1989 | Belzer et al. | |
| 4,879,283 A | 11/1989 | Belzer et al. | |
| 4,994,367 A | 2/1991 | Bode et al. | |
| 5,080,886 A | 1/1992 | Mickle et al. | |
| 5,200,398 A | 4/1993 | Strasberg et al. | |
| 5,370,989 A | 12/1994 | Koga et al. | |
| 5,407,793 A | 4/1995 | Del Nido et al. | |
| 5,498,427 A | 3/1996 | Menasche | |
| 5,552,267 A | 9/1996 | Stern et al. | |
| 5,693,462 A | 12/1997 | Raymond | |
| 5,712,084 A * | 1/1998 | Osgood ...................... | 435/1.2 |
| 5,919,703 A | 7/1999 | Mullen et al. | |

FOREIGN PATENT DOCUMENTS

| | | |
|---|---|---|
| CN | 1178070 A | 4/1998 |
| JP | 06305901 | 11/1994 |
| WO | WO 96/03139 A1 | 2/1996 |

OTHER PUBLICATIONS

Fukuse et al., "Effects of Euro-Collins, University of Wisconsin, and New Extracellular-Type Trehalase-Containing Kyoto Solutions in an Ex Vivo Rat Lung Preservation Model", Transplantation 62 : 1212-1217 (1996).*
Vargas et al., "Postaglandin E1 Attenuation of Ischemic Renal Reperfusion Injury in the Rat", J. Am. Col. Surg. 180 : 713-717 (1995).*
Polyak, M.M.R., et al., Calcium Ion Concentration of Machine Perfusate Predicts Early Graft Function in Expanded Criteria Donor Kidneys, 1999, Transplant International, 12(5):378-382.
Polyak, M., et al., Pulsatile Preservation Characteristics Predict Early Graft Function in Extended Criteria Donor Kidneys, 1997, Transplantation Proceedings 29:3582-3583.
Polyak, M., et al., The Influence of Pulsatile Preservation on Renal Transplantation in the 1990s, 2000, Transplantation 69:249-258.
Polyak, M., et al., Glutathione Supplementation During Cold Ischemia Does Not Confer Early Functional Advantage in Renal Transplantation, 1999, Transplantation, 70(1):202-205.
Polyak, M., et al., Supplemental Reduced Glutathione During Cold Ischemia Does Not Improve Early Renal Allograft Function, 2000, Transplantation Proceedings, 32:32-34.
Polyak, M., et al., Donor Treatment with Phentolamine Mesylate Improves Machine Preservation Dynamics and Early Renal Allograft Function, 1999, Transplantation, 69 (1):184-186.
Polyak, M., et al., The State of Renal Preservation for Transplantation in New York, 1999, Transplantation Proceedings, 31:2091-2093.
Polyak, M., et al., Prostaglandin E1 Influences Pulsatile Preservation Characteristics and Early Graft Function in Expanded Criteria Donor Kidneys, 1999, Journal of Surgical Research, 85:17-25.
Polyak, M., et al., Prostaglandin E1 Improves Pulsatile Preservation Characteristics and Early Graft Function in Expanded Criteria Donor Kidneys, 1998, ASAIO Journal 44:M610-M612.
Polyak, M., et al., Novel Preservation Solution Improves Early Function in the Cold Stored and Machine Preserved Kidney, 2001, American Journal Of Transplantation 1(1), Abstract #1330.
Sun, S.C., et al., Improved Recovery of Heart Transplants by Combined Use of Oxygen-Derived Free Radical Scavenges and Energy Enhancement, Journal of Thoracic and Cardiovascular Surgery, 1992, vol. 104, pp. 830-837.
Le Gal Y.M., et al., Heart-Lung Protection from Ischemiuc Injury during 8 Hour Hypothermic Preservation, Acta Bio-Medica de L'Ateneo Parmense: Organo Della Societa di Medicina e Scienze Naturali di Parma, Italy, 1994, vol. 65, pp. 181-198.
Hiromi, Wada, et al., Effective 30-hour Preservation of Canine Lungs with Modified ET-Kyoto Solution, Annals of Thoracic Surgery, 1996, Issn 0003-4975, vol. 61, pp. 1099-1105.

* cited by examiner

Primary Examiner—Sandra E. Saucier
(74) Attorney, Agent, or Firm—Blank Rome LLP

(57) ABSTRACT

Cold storage solutions for the preservation of organs and biological tissues prior to implantation, including a prostaglandin having vasodilatory, membrane stabilizing, platelet aggregation prevention upon reperfusion, and complement activation inhibitory properties, a nitric oxide donor, and a glutathione-forming agent.

14 Claims, No Drawings

COLD STORAGE SOLUTION FOR ORGAN AND BIOLOGICAL TISSUE PRESERVATION

REFERENCE TO RELATED APPLICATION

This application claims the benefit of U.S. Provisional Application No. 60/240,023 filed on Oct. 13, 2000, entitled "Organ and Biological Tissue Preservation Cold Storage Solution," which is incorporated herein by reference.

FIELD OF INVENTION

The invention relates to the field of organ and biological tissue preservation. In particular, the invention relates to cold storage solutions for the preservation of organs and biological tissues for implant.

BACKGROUND OF INVENTION

It is believed that the ability to preserve human organs for a few days by cold storage after initial flushing with an intracellular electrolyte solution or by pulsatile perfusion with an electrolyte-protein solution has allowed sufficient time for histo-compatibility testing of donor and recipient. It is also believed that preservation by solution or perfusion has also allowed for organ sharing among transplant centers, careful preoperative preparation of the recipient, time for preliminary donor culture results to become available, and vascular repairs of the organ prior to implantation.

It is believed that the 1990's has been a decade characterized by increasing waiting times for cadaveric organs. In renal transplantation, the growing disparity between available donors and patients on the waiting list has stimulated efforts to maximize utilization of cadaveric organs. An obstacle that may arise in the effort to increase utilization is that maximal utilization may require transplantation of all available organs, including extended criteria donor organs. However, by extending the criteria for suitability of donor organs, transplant clinicians may risk a penalty with respect to graft function, diminishing the efficiency of organ utilization if transplanted organs exhibit inferior graft survival. Consequently, interventions that both improve graft function and improve the ability of clinicians to assess the donor organ may be crucial to achieving the goal of maximizing the efficiency of cadaveric transplantation.

The mechanisms of injuries sustained by the cadaveric renal allograft during pre-preservation, cold ischemic preservation and reperfusion are believed to be complex and not fully understood. However, it is believed that there exists ample evidence to suggest that many of the injurious mechanisms occur as a result of the combination of prolonged cold ischemia and reperfusion (I/R). Reperfusion alone may not be deleterious to the graft, since reperfusion after short periods of cold ischemia may be well-tolerated, but reperfusion may be necessary for the manifestation of injuries that originate during deep and prolonged hypothermia. It is suggested that four major components of I/R injury that affect the preserved renal allograft begin during cold ischemia and are expressed during reperfusion. These include endothelial injury, leukocyte sequestration, platelet adhesion and increased coagulation.

Hypothermically-induced injury to the endothelium during preservation may lead to drastic alterations in cytoskeletal and organelle structures. During ischemic stress, profound changes in endothelial cell calcium metabolism may occur. These changes may be marked by the release of calcium from intracellular depots and by the pathological influx of calcium through the plasma membrane. Hypothermic preservation may disrupt the membrane electrical potential gradient, resulting in ion redistribution and uncontrolled circulation of Ca++. The depletion of ATP stored during I/R may compromise ATP-dependent pumps that extrude Ca++ from the cell and the energy intensive shuttle of organelle membranes, causing a dramatic elevation of intracellular free Ca++. Alterations in cytosolic Ca++ concentration may disrupt several intracellular functions, many of which may result in damaging effects. Unregulated calcium homeostasis has been implicated in the development of endothelial and parenchymal injury and is believed to be a fundamental step in the sequelae of steps leading to lethal cell injury. Among the most significant damaging effects of increased cytosolic Ca++ are believed to be the activation of phospholipase A1, 2 and C, the cytotoxic production of reactive oxygen species by macrophages, the activation of proteases that enhance the conversion of xanthine dehydrogenase to xanthine oxidase, and mitochondrial derangements.

Solutions for preserving organs are described in U.S. Pat. Nos. 4,798,824 and 4,879,283, the disclosures of which are incorporated herein in their entirety. One such solution is Viaspan® cold storage solution, which may be used for hypothermic flushing and storage of organs. Despite such solutions, it is believed that there remains a need for organ and tissue preserving solutions that allow for static storage and preservation, while demonstrating superior quality preservation of organ and tissue viability and function.

SUMMARY OF THE INVENTION

The invention provides an organ and tissue preserving solution for static storage preservation that demonstrates superior quality preservation when compared to existing preserving media, in terms of organ and tissue viability and function. The organ and biological tissue preservation aqueous cold storage solution includes a prostaglandin having vasodilatory, membrane stabilizing, platelet aggregation prevention upon reperfusion, and complement activation inhibitory properties, a nitric oxide donor, and a glutathione-forming agent.

The invention also provides a preserved organ or biological tissue comprising a cadaveric organ or tissue within a cold storage solution of the invention in a deep hypothermic condition or physiological condition.

The invention also provides a method for preserving an organ or biological tissue. The method flushes a cadaveric organ or tissue with a cold storage solution of the invention, allows the flushed cadaveric organ or tissue to be enveloped in the cold storage solution, and then stores the cadaveric organ or tissue in the cold storage solution in a deep hypothermic condition or physiological condition.

The invention further provides a method of preparing an organ or biological tissue preservation cold storage solution. The method includes providing a solution with distilled water or deionized water, adding potassium lactobionate, potassium phosphate, raffinose, adenosine, allopurinol, and pentastarch to the solution, and mixing prostaglandin E1, nitroglycerin, and N-acetylcysteine into the solution.

DETAILED DESCRIPTION OF THE INVENTION

In accordance with the invention, the organ and biological tissue preservation aqueous cold storage solution includes a prostaglandin having vasodilatory, membrane stabilizing, platelet aggregation prevention upon reperfusion, and complement activation inhibitory properties, a nitric oxide donor, and a glutathione-forming agent. The organ and biological tissue preservation cold storage solution is intended for infusion into the vasculature of cadaveric and living donor organs for transplantation. Once infused, the donor organs are exsanguinated and blood is replaced by the solution in the native vasculature of the organs to return the organs to a normothermic condition. The solution may be used under deep hypothermic conditions or physiological conditions. The solution remains in the vasculature of the organ, as well as envelops the entire organ during the period of cold ischemia. This method of preservation allows for the extended storage of organs, tissues, and all biological substances. When the organ or tissue is returned to normothermic conditions, the solution is replaced with blood or other physiologic media. Variations of this solution may also be used for machine perfusion preservation. The cold storage solution of the invention may be used in the same manner and for the same tissues and organs as known storage solutions.

A cold storage solution of the invention includes a prostaglandin having vasodilatory, membrane stabilizing, platelet aggregation prevention upon reperfusion, and complement activation inhibitory properties. One such prostaglandin is Prostaglandin E1 (PGE1). PGE1 is an endogenous eicosanoid of the cyclooxygenase pathway and is utilized for its potent vasodilatory properties. In addition, PGE1 has cellular and organelle membrane stabilization properties, cryoprotective properties, and the ability to prevent platelet aggregation upon the vascular endothelium post transplant. As such, PGE1 may inhibit neutrophil adhesion, inhibit neutrophil production of oxygen free radical species, counteract procoagulant activity after endothelial injury, and stabilize cell membranes. When used in vivo, PGE1 is metabolized almost instantaneously by first pass clearance through the lung, but during hypothermic conditions, PGE1 in the cold storage solution may remain vasoactive even after several hours.

A cold storage solution of the invention also contains a nitric oxide donor, such as nitroglycerin. Nitroglycerin is utilized in the solution because of its potent nitric oxide donation properties, its ability to dilate the venous vascular system and prevent vasospasm, and its ability to prevent complement activation upon transplant. Nitroglycerin is known to relax smooth muscle cells of the endothelium, scavenge free oxygen radicals during reperfusion, and prevent the production of such radicals during cold ischemia.

Compounds that form glutathione (glutathione-forming agents) are also components of a cold storage solution of the invention. One such compound is n-acetylcysteine. Glutathione (GSH) is synthesized from L-glutamate, L-cysteine, and glycine in 2 ATP-dependent reactions. The first reaction, known as catalyzed bygamma-glutamylcysteine synthetase, is effectively rate-limited by GSH feedback. The second involves GSH synthetase, which is not subject to feedback by GSH. When GSH is consumed and feedback inhibition is lost, availability of cysteine as a precursor becomes the rate-limiting factor. As such, N-acetylcysteine is proposed to be the only glutathione precursor that can enter the cell freely. In addition, the constitutive glutathione-building properties of N-acetylcysteine help prevent the formation of free oxygen radicals generated during the preservation period and during reperfusion with a recipient's blood.

According to a preferred embodiment of the invention, an organ and biological tissue preservation cold storage solution containing PGE1, nitroglycerin, and N-acetylcysteine in the preserving solution significantly improves vascular resistance, vascular flow, and calcium efflux during the organ preservation period. The inhibition of calcium efflux over time in kidneys preserved by the proposed solution suggests that, in addition to vasoactive effects, an additional cytoprotective and cryoprotective effect may also be important in ameliorating ischemic injury. These improvements are substantiated ultrastructurally by improved appearance of mitochondria in proximal tubular cells compared to mitochondria from kidneys not exposed to the proposed solution.

A cold storage solution of the invention may also contain components that are typically used in known cold storage solutions. See, U.S. Pat. Nos. 4,798,824 and 4,879,283. For example, other components that may be utilized in the solution include: potassium lactobionate, which is an impermeant anion that reduces cell swelling, $KH_2PO_4$, which provides acid-base buffering and maintains the pH of the solution, $MgSO_4$, which stabilizes cellular and organelle membranes, and raffinose, which is a complex sugar that reduces cell swelling and provides energy stores for metabolically stressed cells. In addition, adenosine, which is a precursor to ATP synthesis, allopurinol, which is a free oxygen radical scavenger, and pentastarch, which is an oncotic supporter, may be added to the solution. NaCl and KOH may also be used for acid-base buffering and maintenance of the pH of the solution.

In a preferred embodiment, the organ or biological tissue preservation cold storage solution includes, but is not limited to:

TABLE 1

| COMPOSITION | AMOUNT IN 1 LITER |
| --- | --- |
| Potassium Lactobionate | 50–150 mM |
| $KH_2PO_4$ | 10–40 mM |
| $MgSO_4$ | 2–8 mM |
| Raffinose | 10–50 mM |
| Adenosine | 1–20 mM |
| Allopurinol | 1–10 mM |
| Pentastarch | 40–60 g/L |
| Prostaglandin E1 | 100–5,000 mcg/L |
| Nitroglycerin | 1–10 mg/L |
| N-Acetylcysteine | 0.1–4 mg/L |
| Sterile Water | 700–900 mL |

In a more preferred embodiment, the organ or biological tissue preservation cold storage solution includes, but is not limited to:

TABLE 2

| COMPOSITION | AMOUNT IN 1 LITER |
| --- | --- |
| Potassium Lactobionate | 75–125 mM |
| $KH_2PO_4$ | 20–30 mM |
| $MgSO_4$ | 3–7 mM |
| Raffinose | 20–40 mM |
| Adenosine | 2–10 mM |
| Allopurinol | 1–5 mM |
| Pentastarch | 45–55 g/L |
| Prostaglandin E1 | 250–3,000 mcg/L |
| Nitroglycerin | 2–7 mg/L |
| N-Acetylcysteine | 0.5–2 mg/L |
| Sterile Water | 700–900 mL |

In a most preferred embodiment, the organ or biological tissue preservation cold storage solution includes, but is not limited to:

TABLE 3

| COMPOSITION | AMOUNT IN 1 LITER |
| --- | --- |
| Potassium Lactobionate | 100 mM |
| $KH_2PO_4$ | 25 mM |
| $MgSO_4$ | 5 mM |
| Raffinose | 30 mM |
| Adenosine | 5 mM |
| Allopurinol | 1 mM |
| Pentastarch | 50 g/L |
| Prostaglandin E1 | 500 mcg/L |
| Nitroglycerin | 5 mg/L |
| N-Acetylcysteine | 1 mg/L |
| Sterile Water | 800 mL |

A cold storage solution of the invention may be prepared by combining the components described above with sterile water, such as distilled and/or deionized water. For example, to prepare the organ and biological tissue preservation cold storage solution, approximately 700–900 mL, or preferably about 800 mL, of sterile water is poured into a one liter beaker at approximately room temperature. Although a one liter beaker is used in this example, any other container of any size may be used to prepare the solution, where the component amounts would be adjusted accordingly. In the most preferred embodiment, the following are added, in any order, to the solution and each is mixed until dissolved in the solution: approximately 100 mol/L of potassium lactobionate, approximately 25 mol/L of potassium phosphate, approximately 30 mol/L of raffinose, approximately 5 mol/L of adenosine, approximately 1 mol/L of allopurinol and approximately 50 g of modified pentastarch. The modified pentastarch is a fractionated colloid mixture of 40–60 kDaltons in diameter and is modified by infusing the pentastarch under 3 atm of pressure through a dialyzing filter with a bore size of about 40–60 kDaltons. Then, in a second step, approximately 500 mcg of modified prostaglandin E1 (PGE1), approximately 5 mg nitroglycerin, and approximately 1 mg of N-acetylcysteine, are added, in any order, to the solution. PGE1 is modified by centrifuging PGE1 under hypothermic conditions at 30K rpm and then filtering the resulting mixture through a 0.05 micro filter. The modified PGE1 has a half-life lengthened by a multiple of about 15. The first and second step may also be reversed.

The invention also provides a method for preserving an organ or biological tissue. The method flushes a cadaveric organ or tissue with a cold storage solution of the invention, allows the flushed cadaveric organ or tissue to be enveloped in the cold storage solution, and then stores the cadaveric organ or tissue in the cold storage solution in a deep hypothermic condition or physiological condition. Additional cold storage solution may be added to ensure adequate preservation of the organ or tissue. Preferred temperatures range from about 2–10° C. in the deep hypothermic condition and are about 37° C., or room temperature, in the physiological condition. In one embodiment, the cold storage solution is first cooled to below 10° C. using an ice bath or other cooling means known in the art. It is typical to inspect the cooled solution for any precipitates which may be removed by filtration prior to use. Alternatively, the organ or tissue to be preserved may be placed in the solution and then cooled.

The invention further provides a preserved organ or biological tissue comprising a cadaveric organ or tissue within a cold storage solution of the invention in a deep hypothermic condition or physiological condition. As discussed above, preferred temperatures range from about 2–10° C. in the deep hypothermic condition and are about 37° C., or room temperature, in the physiological condition.

The invention is further explained by the following of examples of the invention as well as comparison examples. In all of the examples, kidneys were procured from heart-beating donors and preserved in a laboratory by cold storage preservation. Randomization was accomplished as an open labeled, sequential analysis. All agents were added immediately prior to vascular flush.

Data Collected

The following donor, preservation, and postoperative recipient outcome data were collected for either Example 1 or 2: donor age (D age, years), final donor creatinine (D Cr, mg/dL), donor intraoperative urine output (U/O, mL), cold ischemic time (CIT, hours), perfusion time (PT, hours), perfusate [Na+] (mM/100 g), perfusate [Cl–] (mM/100 g), perfusate [K+] (mM/100 g), perfusate [Ca++] (mM/100 g), perfusate pH, renal flow during MP (FL, mL/min/100 g), renal resistance during MP (RES, mmHg/(mL/min/100 g), recipient age (R age, years), recipient discharge creatinine (R Cr, mg/dL), initial length of recipient hospital stay (LOS, days), immediate graft function (IF, %) defined as urine production exceeding 2000 mL during the first 24 postoperative hours, delayed renal allograft graft function (DGF, %) defined as the need for dialysis within the first 7 days post-transplant, and present function (3 Mo or 1 Yr, %) defined as 3 month or one year post-operative graft status.

Method of Preservation

All cold stored kidneys subject to the above criteria were flushed and cold stored at 4° C. in 1 L of either University of Wisconsin (UW) solution (Viaspan® cold storage solution, Dupont Pharma, Wilmington, De.) or the Cold Organ Storage (Perfusion) solution (OPS) of the present invention. The University of Wisconsin solution, which is also the Control-UW solution, is described in U.S. Pat. Nos. 4,798,824 and 4,879,283.

Statistical analysis

All data are reported as mean values ±SEM unless otherwise noted. Paired and unpaired student's t-tests were used where appropriate. All statistical analyses were performed by Statview 4.5 software (Abacus Concepts, Berkeley, Calif.).

EXAMPLE 1

Comparison of selected donor, preservation, and outcome variables by method and type of organ preservation solution (mean +/– SEM)
n = number of recipients
ns = not significant

| | OPS (n = 70) | University of Wisconsin (n = 62) | p value (unpaired Student's t-test) |
| --- | --- | --- | --- |
| Donor characteristics | | | |
| Donor age (y) | 41.2 | 39.8 | ns |
| Final serum creatinine(mg/dl) | 1.0 | 1.0 | ns |
| Preservation characteristics | | | |
| Cold ischemic time (h) | 23 | 23 | ns |
| Outcome characteristics | | | |
| Delayed graft function (%) | 19 | 31 | 0.04 |
| 1 yr. graft survival (%) | 98 | 94 | ns |

EXAMPLE 2

Comparison of selected donor, preservation, and outcome characteristics by type of organ preservation solution - cold storage formulation (mean +/−SEM)
PGE1 = prostaglandin E1 (500 mcg/L)
NTG = Nitroglycerin (5 mg/L)
n = number of recipients

|  | PGE1 (n = 48) | NTG (n = 67) | PGE1 + NTG (n = 65) (Embodiment of Table 3) | Control-UW solution (n = 86) | p value (unpaired student's t-test) |
|---|---|---|---|---|---|
| Donor Characteristics |  |  |  |  |  |
| Donor age (y) | 38.5+/−7 | 38.5+/−9 | 41.4+/−8 | 44.0+/−12 | 0.8 |
| Final serum creatinine (mg/dl) | 1.0+/−0.2 | 1.3+/−0.4 | 0.8+/−0.5 | 0.9+/−0.5 | 0.65 |
| Intraoperative urine output (ml) | 300+/−90 | 290+/−120 | 280+/−70 | 200+/−80 | 0.45 |
| Preservation characteristics |  |  |  |  |  |
| Cold ischemic time (h) | 22+/−5 | 23+/−6 | 24+/−5 | 23+/−4 | 0.59 |
| Outcome characteristics |  |  |  |  |  |
| Immediate function (%) | 84+/−4 | 82+/−3 | 84+/−6 | 77+/−5 |  |
| Delayed grant function (%) | 16+/−5 | 18+/−3 | 15+/−4 | 22+/−5 |  |
| 3 month function (%) | 95+/−3 | 90+/−5 | 94+/−4 | 87+/−5 |  |

While the invention has been disclosed with reference to certain preferred embodiments, numerous modifications, alterations, and changes to the described embodiments are possible without departing from the sphere and scope of the invention, as defined in the appended claims and their equivalents thereof. For example, although the detailed description may refer, at times, to only organs, the terms "organs" and "organ" encompass all organs, tissues and body parts that may be transplanted. Accordingly, it is intended that the invention not be limited to the described embodiments, but that it have the full scope defined by the language of the following claims.

What we claim is:

1. An organ or biological tissue preservation aqueous cold storage solution comprising:
   about 1,000 micrograms/L prostaglandin E1,
   about 10 mg/L nitroglycerin,
   about 0.2 mg/L N-acetylcysteine,
   about 50–150 mM potassium lactobionate,
   about 10–40 mM $KH_2PO_4$,
   about 2–8 mM $MgSO_4$,
   about 10–50 mM raffinose,
   about 1–20 mM adenosine,
   about 1–10 mM allopurinol, and
   about 40–60 g/L pentastarch.

2. An organ or biological tissue preservation aqueous cold storage solution comprising:
   about 1,000 micrograms/L prostaglandin E1,
   about 10 mg/L nitroglycerin,
   about 0.2 mg/L N-acetylcysteine,
   about 75–125 mM potassium lactobionate,
   about 20–30 mM $KH_2PO_4$,
   about 3–7 mM $MgSO_4$,
   about 20–40 mM raffinose,
   about 2–10 mM adenosine,
   about 1–5 mM allopurinol, and
   about 45–55 g/L pentastarch.

3. An organ or biological tissue preservation aqueous cold storage solution comprising:
   about 1,000 micrograms/L prostaglandin E1,
   about 10 mg/L nitroglycerin,
   about 0.2 mg/L N-acetylcysteine,
   about 100 mM potassium lactobionate,
   about 25 mM $KH_2PO_4$,
   about 5 mM $MgSO_4$,
   about 30 mM raffinose,
   about 5 mM adenosine,
   about 1 mM allopurinol, and
   about 50 g/L pentastarch.

4. The cold storage solution of claims 1, 2, or 3, further comprising NaCl and KOH.

5. The cold storage solution of claim 1, further comprising sterile water.

6. The cold storage solution of claim 5, further comprising about 700–900 mls sterile water.

7. A method for preserving an organ or biological tissue comprising:
   flushing at least one of a cadaveric organ and tissue with the cold storage solution of claim 1, 2 or 3;
   allowing the flushed at least one of a cadaveric organ and tissue to be enveloped in the cold storage solution; and
   storing the at least one of a cadaveric organ and tissue in the cold storage solution in at least one of a deep hypothermic condition and physiological condition.

8. The method of claim 7 wherein the flushing comprises:
   infusing the solution into vasculature of the at least one of a cadaveric organ and tissue; and exsanguinating the at least one of a cadaveric organ and tissue.

9. The method of claim 7 wherein the storing comprises:
replacing blood in vasculature of the at least one of a cadaveric organ and tissue with the solution.

10. The method of claim 7 further comprising:
replacing the solution with at least blood to return the at least one of a cadaveric organ and tissue to a normothermic condition.

11. The method of claim 7 further comprising:
cooling the solution to below 10° C.;
inspecting the cooled solution for precipitates; and
removing any precipitates by filtration.

12. A method of preparing the organ or biological tissue preservation solution of claim 1, 2 or 3 comprising:
providing a solution with sterile water;
adding the potassium lactobionate, the potassium phosphate, the raffinose, the adenosine, the allopurinol and the pentastarch to the solution; and
mixing the prostaglandin E1, the nitroglycerin and the N-acetylcysteine into the solution.

13. The method of claim 12 further comprising:
mixing the solution until all components are dissolved.

14. The method of claim 12 further comprising:
infusing the pentastarch under pressure through a dialyzing filter;
centrifuging the prostaglandin E1 under hypothermic conditions; and
filtering the centrifuged prostaglandin E1.

* * * * *